(12) United States Patent
Brelvi et al.

(10) Patent No.: US 10,786,269 B1
(45) Date of Patent: Sep. 29, 2020

(54) DISPOSABLE SNARE AND RETRIEVAL DEVICE AND ASSOCIATED METHOD

(76) Inventors: Zamir Brelvi, Montville, NJ (US); Kamal Dutta, Montville, NJ (US)

( * ) Notice: Subject to any disclaimer, the term of this patent is extended or adjusted under 35 U.S.C. 154(b) by 0 days.

(21) Appl. No.: 13/438,906

(22) Filed: Apr. 4, 2012

(51) Int. Cl.
 *A61B 17/221* (2006.01)
 *A61B 17/22* (2006.01)
 *A61B 17/3205* (2006.01)

(52) U.S. Cl.
 CPC ...... *A61B 17/221* (2013.01); *A61B 17/32056* (2013.01); *A61B 17/22031* (2013.01); *A61B 2017/2212* (2013.01); *A61B 2017/2217* (2013.01)

(58) Field of Classification Search
 CPC .......... A61B 17/221; A61B 2017/2212; A61B 17/22031; A61B 2017/2217; A61B 17/32056
 USPC .................................. 606/110, 113
 See application file for complete search history.

(56) References Cited

U.S. PATENT DOCUMENTS

| | | | | |
|---|---|---|---|---|
| 3,955,578 A | * | 5/1976 | Chamness | A61B 17/32056 606/47 |
| 5,354,303 A | * | 10/1994 | Spaeth | A61B 17/00234 604/171 |
| 6,015,415 A | | 1/2000 | Avellanet | |
| 6,814,739 B2 | * | 11/2004 | Secrest et al. | 606/114 |
| 7,044,947 B2 | | 5/2006 | de la Torre | |
| 7,052,495 B2 | | 5/2006 | Smith | |
| 8,043,303 B2 | * | 10/2011 | Razvi et al. | 606/113 |
| 2011/0106107 A1 | * | 5/2011 | Binmoeller | A61B 17/0487 606/139 |

* cited by examiner

*Primary Examiner* — Elizabeth Houston
*Assistant Examiner* — Michael G Mendoza
(74) *Attorney, Agent, or Firm* — Ashkan Najafi

(57) ABSTRACT

A snare and retrieval device including a handle section, a cord section attached to the handle section, and a tip section removably attached to the cord section and spaced away from the handle section. Such a tip section is selectively detachable from the cord section while the cord section remains attached to the handle section. The tip section is detachable thereby allowing a surgeon to easily change the snare tip to a bigger or smaller size as necessary during the operation. A user can use one cord section for both removal of a polyp followed by retrieval of the polyp for further examination. This is done by changing the snare member to a retrieval member. The detachability of the tip section allows the device to replace at least two or more separate snare and retrieval devices, thereby reducing cost and time during the operation.

6 Claims, 10 Drawing Sheets

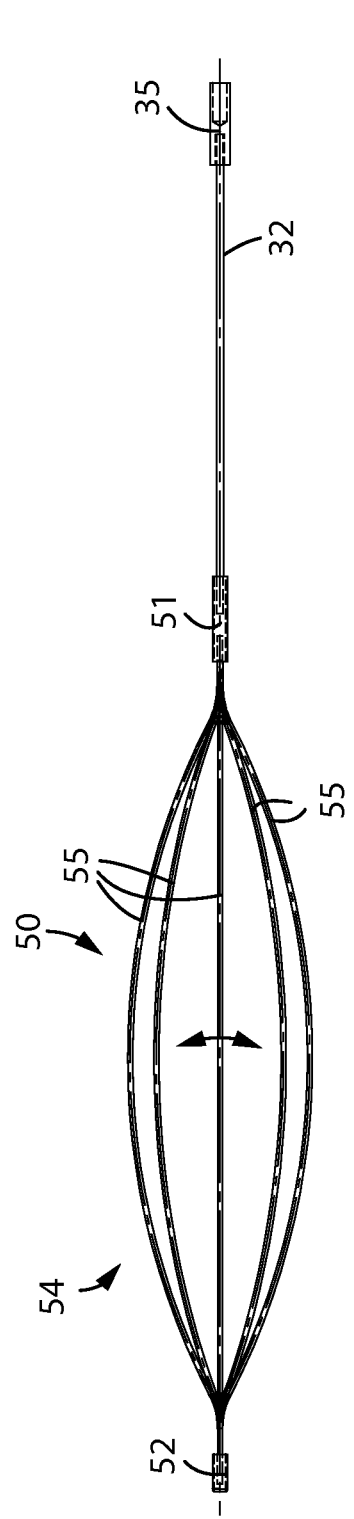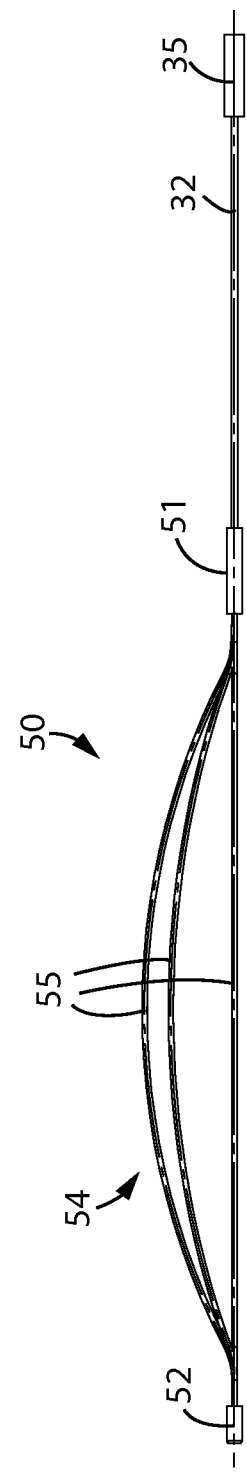

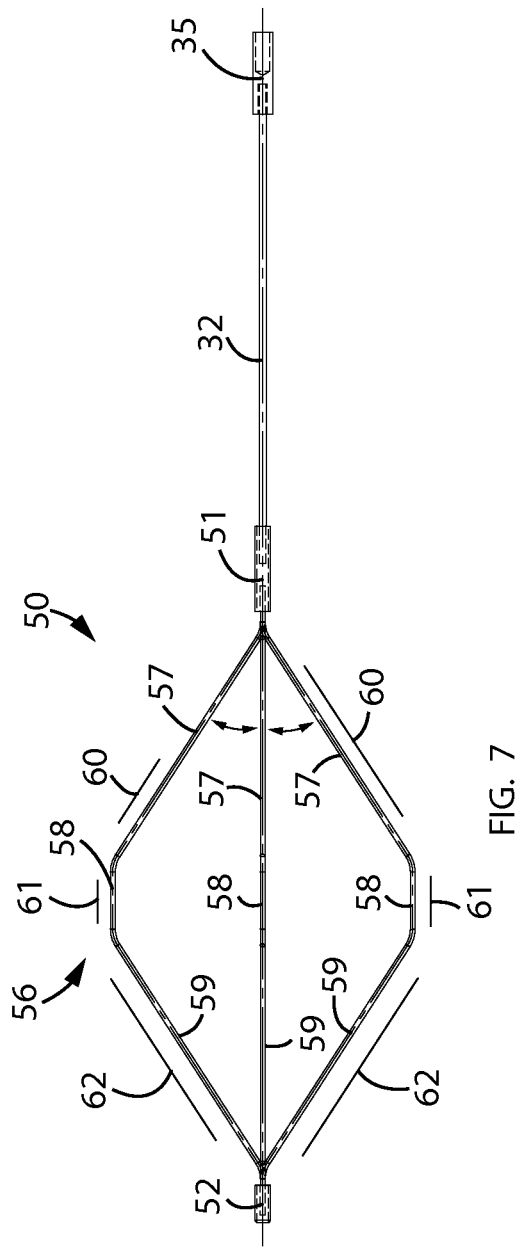
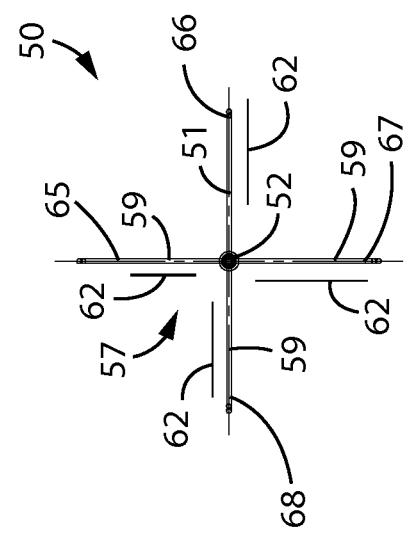
FIG. 7
FIG. 8

DISPOSABLE SNARE AND RETRIEVAL DEVICE AND ASSOCIATED METHOD

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

Technical Field

This disclosure relates to surgical instruments and, more particularly, to a disposable snare and retrieval device for providing users with an easy and convenient means of removing polyps or other foreign objects from a colon.

Prior Art

Colonoscopy is the minimally invasive, endoscopic examination of the large colon and the distal part of the small bowel with a fiber optic "camera" on a flexible tube passed through the anus. It may provide a visual diagnosis (e.g. ulceration, polyps), and offers physicians the opportunity to sample and retrieve suspicious lesions for biopsy. Colonoscopy allows a complete examination of the colon, which can measure well over six feet in overall length. Frequently used to detect or rule out colon cancer, colonoscopy is also used to detect inflammatory bowel disease. Due to the high mortality associated with colon cancer and the high effectiveness and low risk associated with colonoscopy, it is now also becoming a routine screening test for people 50 years of age or older.

The endoscopes used in colonoscopy come in two types. The original purely fiber-optic instrument has a flexible bundle of glass fibers that collects the lighted image at one end and transfers the image to the eye piece. The newer video endoscopes use a tiny, optically sensitive computer chip at the end. Electronic signals are then transmitted up the scope to a computer which displays the image on a large video screen. Both varieties of endoscope feature a movable tip and multiple channels for instrumentation, air, suction and light. These channels allow the physician to insert the appropriate instrument into the endoscope, run it through the scope to the site of interest, and operate the instrument either electronically or manually, by means of a long connecting wire sheathed in a thin, TEFLON® coated steel cable.

In this manner, suspicious lesions may be cauterized, treated with laser light or snared and retrieved for further examination. The snare and retrieval devices currently employed on endoscopes are routinely used, then cleaned and sterilized for continued use. The instruments themselves are well designed and dependable. Another limitation of the currently used devices is the need to change the entire device between removal of a polyp and retrieval of a polyp. Also, there are situations especially during removal of foreign bodies from the gastrointestinal tract that one type of retrieval device is not suitable. This causes a need for using multiple devices costing money and precious time. Currently, conventional devices are available as "disposable" where the entire device is disposed. Other conventional devices are "reusable" in which case the devices can be reused after proper cleaning and sterilization.

Another limitation of the currently used devices is the need to change the entire device between removal of a polyp and retrieval of a polyp. Retrieval devices are used when the polyp is too large to come out through the suction channel of the endoscope.

Also, sometimes there are situations especially during the removal of foreign bodies from the gastrointestinal tract that one type of retrieval device is not suitable. For example if a child has accidentally swallowed a coin and an AAA battery. In this case multiple retrieval devices may be needed to remove these foreign bodies such as a basket for the coin and a grasper for the battery costing more money and time during the operation. Currently the devices are available as "disposable" where the entire device is disposed. The devices are also "reusable in which case the devices can be reused after proper cleaning and sterilization.

Accordingly, a need remains for an apparatus in order to overcome the above-noted shortcomings. The present disclosure satisfies such a need by providing a disposal snare and retrieval device that is convenient and easy to use, lightweight yet durable in design, versatile in its applications, and designed for removing a polyp or foreign object from a colon.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a snare and retrieval device for removing an internal object from a patient. In conventional snare and retrieval devices, the snare loop or retrieval tip is not detachable from the activating cable or cord. Therefore, if a different snare member and/or retrieval member is needed the entire device has to be changed. The present disclosure overcomes such a shortcoming.

These and other objects, features, and advantages of the non-limiting exemplary embodiment(s) are provided by the snare and retrieval device including a handle section, a cord section attached to the handle section, and a tip section removably attached to the cord section and spaced away from the handle section. Such a tip section is selectively detachable from the cord section while the cord section remains attached to the handle section.

In a non-limiting exemplary embodiment, the handle section preferably includes a base member, and an elongated arm passing through the base member and connected to the cord section. Such an elongated arm is linearly reciprocated relative to the base member and thereby causing reciprocation of at least a portion of the cord section and the tip section.

In a non-limiting exemplary embodiment, the cord section preferably includes a flexible cord having first and second cord portions, a flexible sheath removably mated to the base member and surrounding the first cord portion. Such a first cord portion is connected to the elongated arm and is caused to reciprocate within the flexible sheath when the elongated arm is reciprocated through the base member.

In a non-limiting exemplary embodiment, the cord section further includes a first cord portion coupling removably connected to a distal end of the first cord portion, a second cord portion coupling removably connected to the first cord portion coupling and the second cord portion. Such a second cord portion coupling is intercalated between the first cord portion coupling and the second cord portion.

In a non-limiting exemplary embodiment, the first cord portion coupling includes a body having a female portion provided with a first axial bore formed therein, a male portion connected to the female portion. Such a male portion axially protrudes outwardly away from the first axial bore. The second cord portion coupling preferably includes a body having a second axial bore and a third axial bore extending inwardly from proximal and distal ends thereof respectively. The second axial bore is spaced from the third axial bore. In this manner, the male portion is removably connected to the second axial bore such that alternate ones of the tip section are selectively connected to the cord section without having to discard the cord section and the handle section.

In a non-limiting exemplary embodiment, the tip section includes a tip section coupling attached to a distal end of the second cord portion, and at least one of a retrieval member and a snare member removably connected to the tip section coupling.

In a non-limiting exemplary embodiment, the retrieval member include at least one basket selected from a group including a mesh basket and a wire basket, and an end cap attached to a distal end of the wire basket.

In a non-limiting exemplary embodiment, the wire basket includes at least one of: a plurality of arcuate wires engaged at opposed proximal and distal ends thereof such that the arcuate wires form a bowed shape, and a plurality of bent wires engaged at opposed proximal and distal ends thereof. Each of such bent wires has first, second and third linear sections registered in respectively first, second and third paths such that oppositely facing ones of the second linear sections are registered parallel to each other, respectively.

In a non-limiting exemplary embodiment, the snare member includes at least one of: a plurality of elongated elements conjoined at the tip section coupling and spanning outwardly away therefrom wherein each of the elongated elements has a loop formed at a distal end of the tip section, and an elongated member having a substantially oval shape wherein proximal and distal ends of the oval shape are pinched inwardly.

The present discourse further includes a method of utilizing a snare and retrieval device for removing an internal object from a patient, the method including the steps of: providing a handle section; providing and attaching a cord section to the handle section; providing and removably attaching a tip section to the cord section such that the tip section is spaced away from the handle section; and using the tip section to detach a polyp from the patient.

Such a method further includes the steps of: selectively detaching the tip section from the cord section while the cord section remains attached to the handle section; attaching an alternate one of the tip section to the cord section; and using the alternate tip section to retrieve the polyp from the patient.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

FIG. 1a is an enlarged view showing an exemplary detachable connection between a cable and a retrieval section identified in FIG. 1;

FIG. 5 is a top plan view showing another exemplary retrieval basket removably attached to the cable end of the device;

FIG. 6 is a side elevational view of the exemplary retrieval basket shown in FIG. 5;

FIG. 7 is a top plan view showing yet another exemplary retrieval basket removably attached to the cable end of the device;

FIG. 8 is a side elevational view of the exemplary retrieval basket shown in FIG. 7;

FIG. 11a is an enlarged top plan view of a resilient proximal end of the exemplary grasper shown in FIG. 11;

FIG. 11b is an enlarged top plan view of a resilient distal end of the exemplary grasper shown in FIG. 11;

Figure 1:
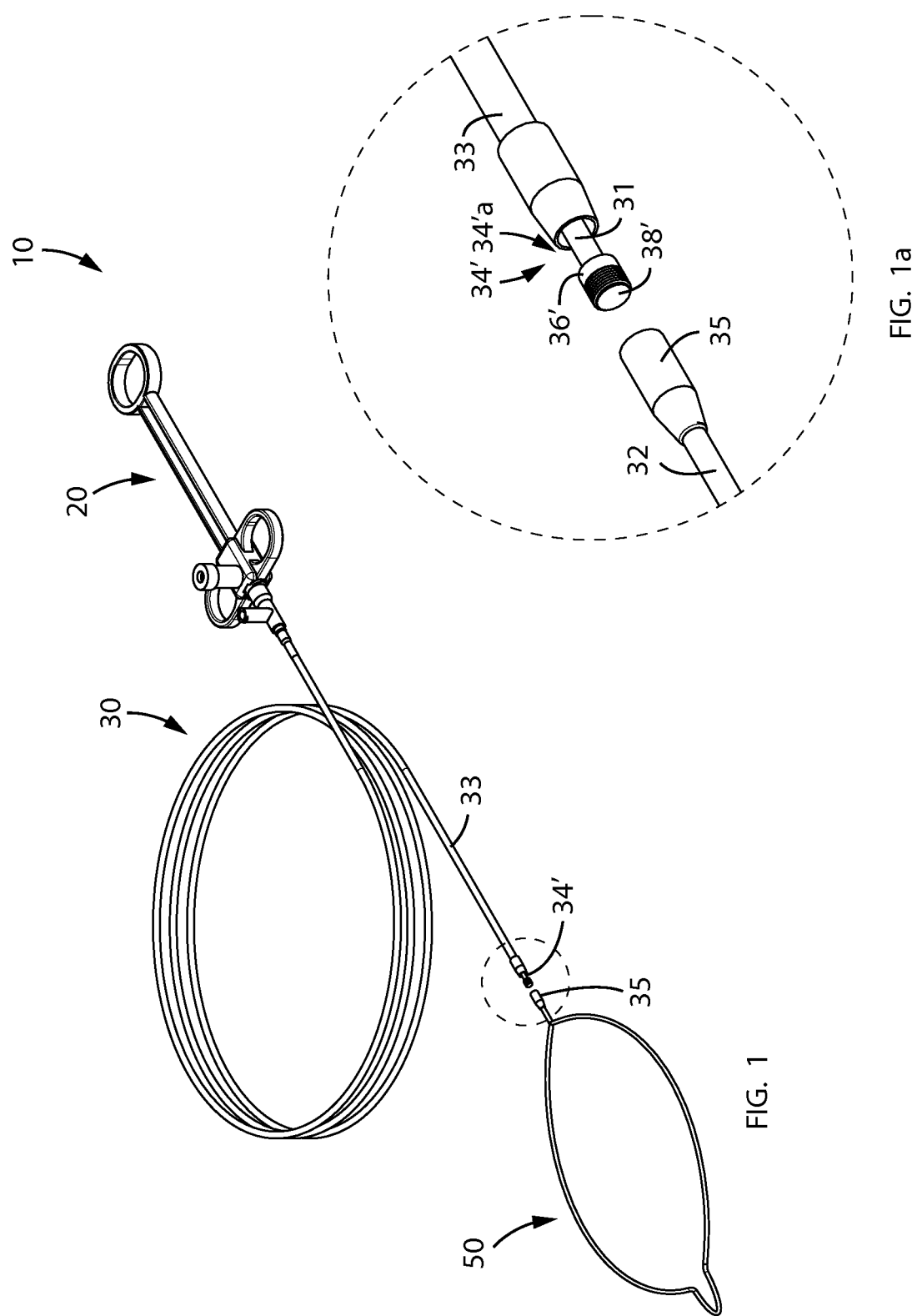
FIG. 1 is a perspective view showing a disposable snare and retrieval device, in accordance with a non-limiting exemplary embodiment.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, devices and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

The non-limiting exemplary embodiment(s) is/are referred to generally in FIGS. 1-16 and is/are intended to provide a snare and retrieval device 10. It should be understood that such non-limiting exemplary embodiment(s) may be used to detach/remove various internal objects from a patient, and should not be limited to detaching/removing only polyps.

Referring to FIGS. 1-16, a snare and retrieval device 10 for removing an internal object (e.g., polyp) from a patient includes a handle section 20, a cord section 30 attached to the handle section 20, and a tip section 50 removably attached to the cord section 30, and spaced away from the handle section 20. Such a tip section 50 is selectively detachable from the cord section 30 while the cord section 30 remains attached to the handle section 20. Such a structural configuration provides the unexpected and unpredictable advantage of enabling a user to quickly and efficiently change one tip section 50 for another tip section 50 without having to obtain a new device.

In a non-limiting exemplary embodiment, the handle section 20 preferably includes a base member 21, and an elongated arm 22 passing through the base member 21, and connected to the cord section 30. Such an elongated arm 22 is linearly reciprocated relative to the base member 21 and thereby causes reciprocation of at least a portion (e.g., first and/or second cord portions 31, 32) of the cord section 30 and the tip section 50. Such a structural configuration provides the unexpected and unpredictable advantage of permitting a user to retract and extend the cord section 30 as needed with a variety of detachable tip sections 50 interchangeably mated to the cord section 30.

In a non-limiting exemplary embodiment, the cord section 30 preferably includes a flexible cord (collectively at 31, 32) having first and second cord portion 31, 32, a flexible sheath 33 removably mated to the base member 21, and surrounding at least the first cord portion 31. Such a first cord portion 31 is connected to the elongated arm 22 and is caused to reciprocate within the flexible sheath 33 when the elongated arm 22 is reciprocated through the base member 21. Such a structural configuration provides the unexpected and unpredictable advantage of retracting and extending the cord section 30 as needed, thereby expanding/contracting the tip section 50 during removal/insertion processes, respectively.

Figure 2:
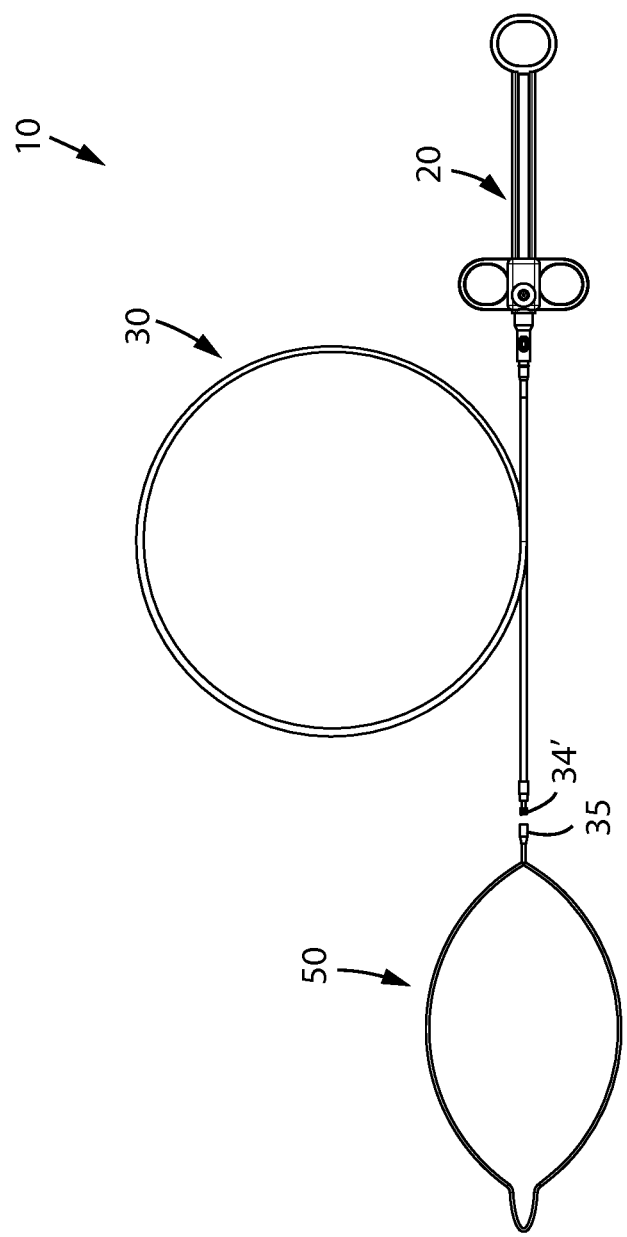
FIG. 2 is a top plan view showing a disposable snare and retrieval device shown in FIG. 1.
Figure 3:
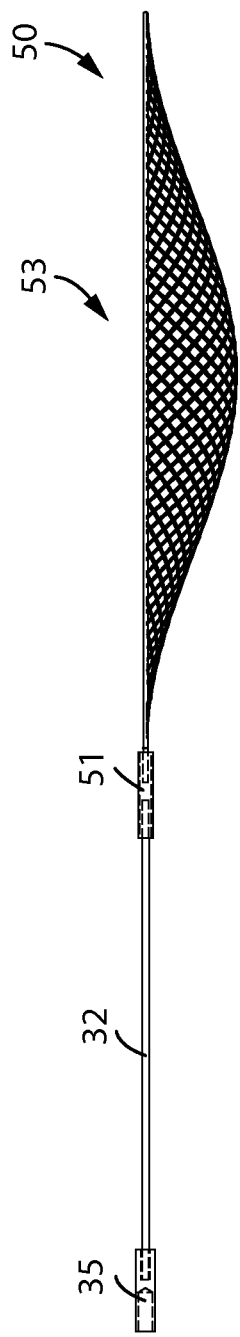
FIG. 3 is a side elevational view showing one exemplary retrieval basket removably attached to a cable end of the device.
Figure 4:
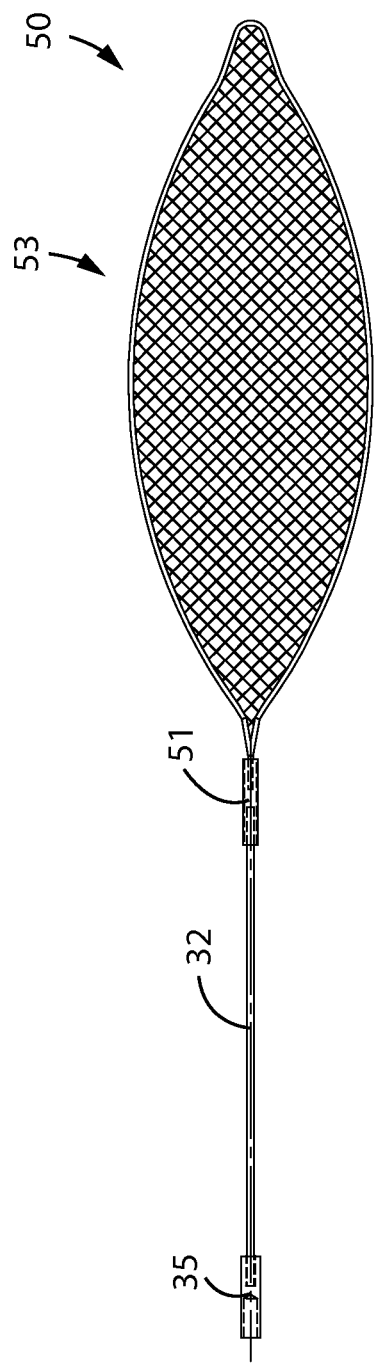
FIG. 4 is a top plan view of the retrieval basket shown in FIG. 3.
Figure 9:
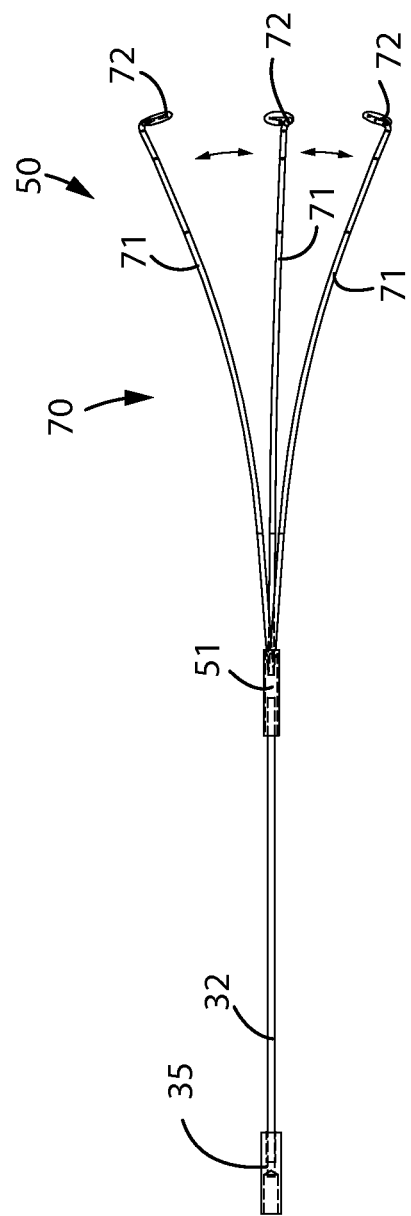
FIG. 9 is a top plan view showing an exemplary grasper removably attached to the cable end of the device.
Figure 10:
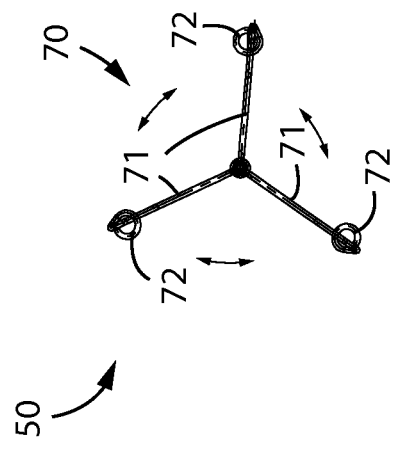
FIG. 10 is a side elevational view of the exemplary grasper shown in FIG. 9.
Figure 11:
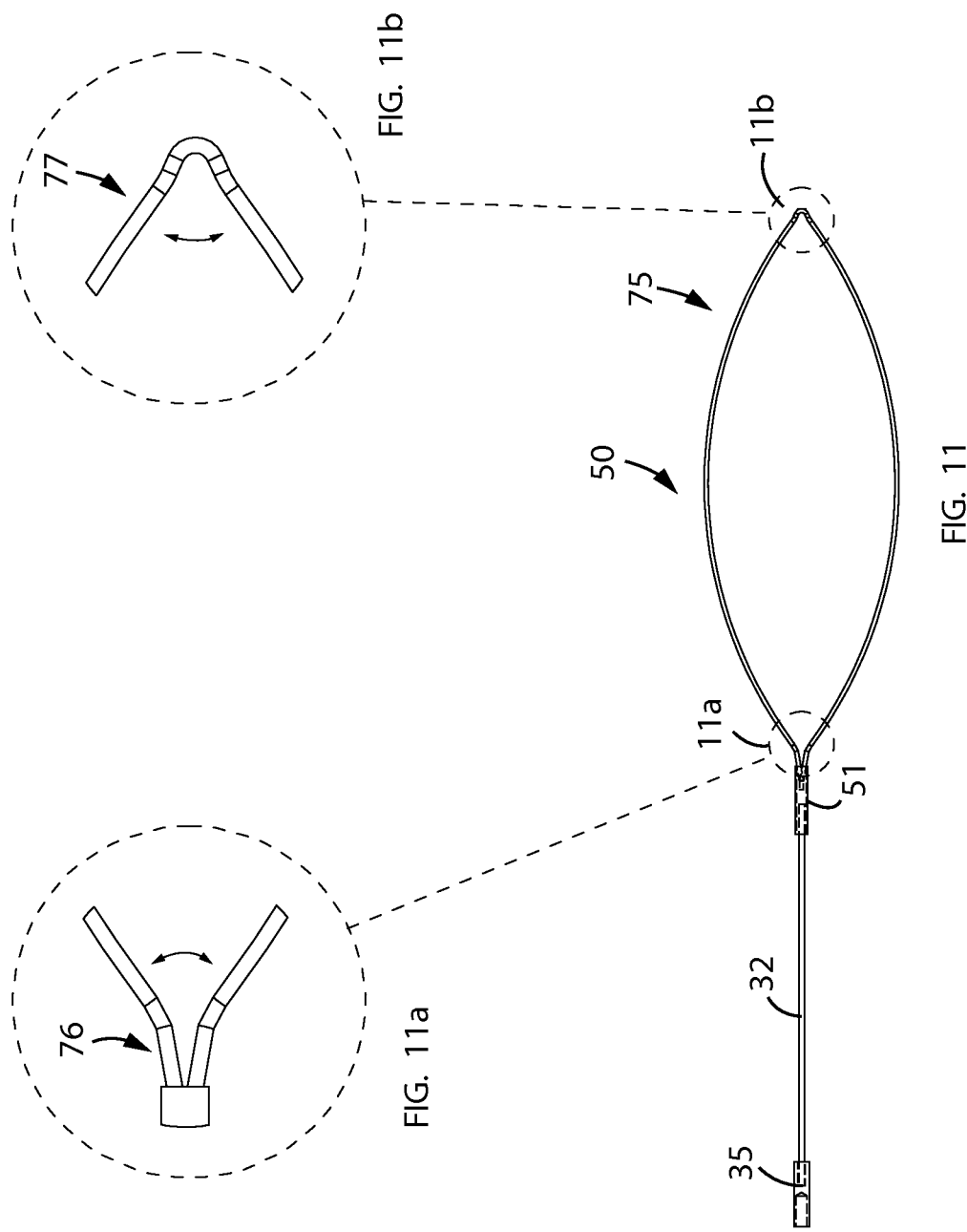
FIG. 11 is a top plan view showing yet another exemplary grasper removably attached to the cable end of the device.
Figure 12:
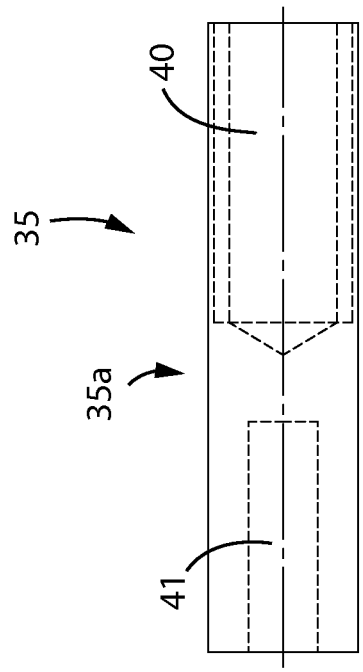
FIG. 12 is a side elevational view of an exemplary tip section coupling for attaching the retrieval section of the device to the cable section.
Figure 13:
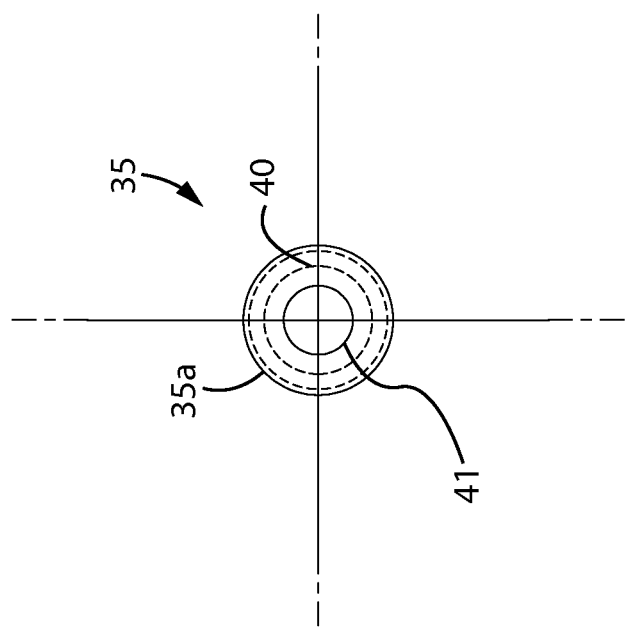
FIG. 13 is an end view of the exemplary tip section coupling shown in FIG. 12.
Figure 14:
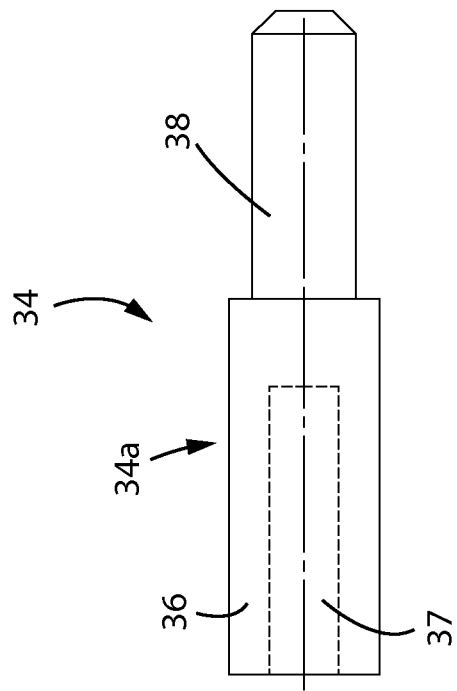
FIG. 14 is a side elevational view of an exemplary cord section coupling for removably attaching the cable section to the tip section coupling shown in FIGS. 12 and 13.
Figure 15:
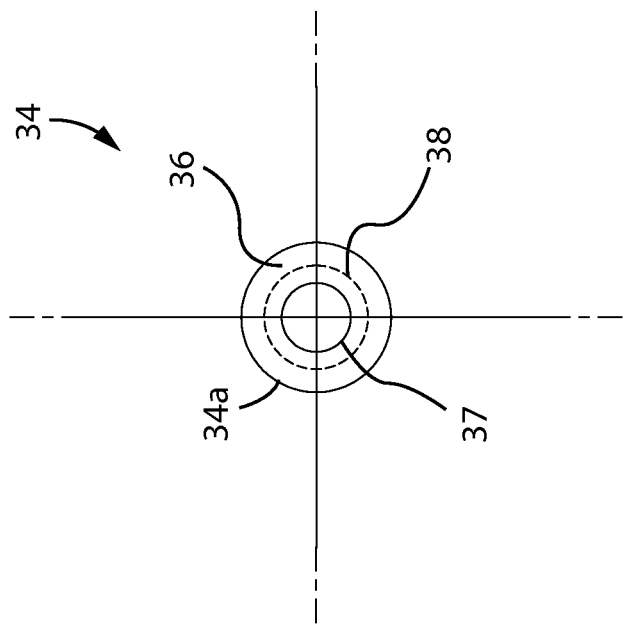
FIG. 15 is an end view of the exemplary cord section coupling shown in FIG. 14.
Figure 16:
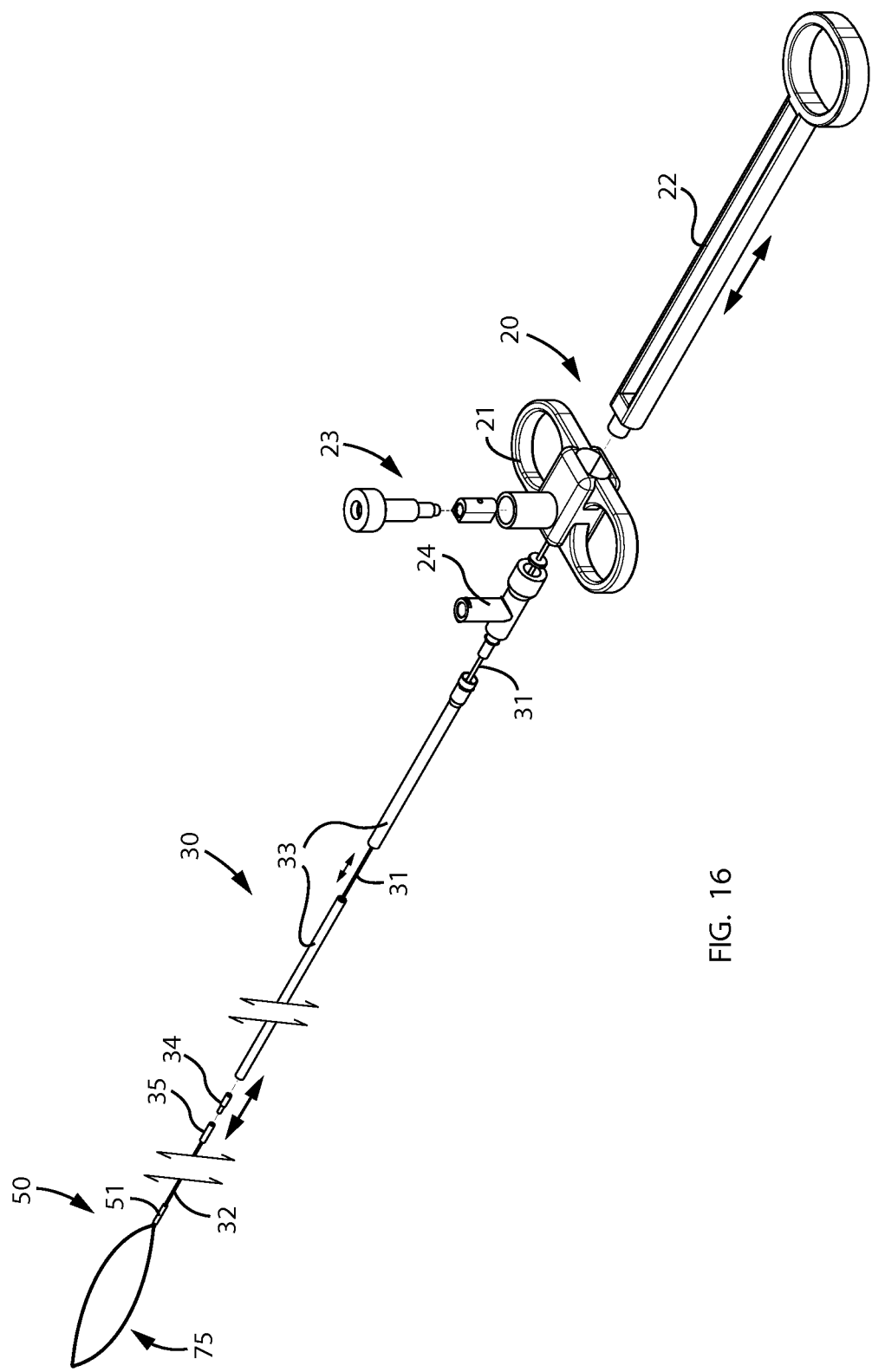
FIG. 16 is an exploded view of another exemplary snare and retrieval device, in accordance with a non-limiting exemplary embodiment.

In a non-limiting exemplary embodiment, the cord section 30 further includes a first cord portion coupling 34, 34' (it is noted that FIGS. 1-2 show a first embodiment of the first cord portion coupling 34 and FIGS. 14-16 show a second embodiment of the first cord portion coupling 34) removably connected to a distal end of the first cord portion 31. A second cord portion coupling 35 is removably connected to the first cord portion coupling 34, 34' and the second cord portion 32. Such a second cord portion coupling 35 is intercalated between the first cord portion coupling 34, 34' and the second cord portion 32. Such a structural configuration provides the unexpected and unpredictable advantage of enabling a user to quickly and efficiently change one tip section 50 for another by merely disconnecting the first 34, 34' and second 35 cord portions couplings, as needed.

Referring to FIGS. 1-2 and 12-16, in a non-limiting exemplary embodiment, the first cord portion coupling 34, 34' includes a body 34a, 34'a having a female portion 36, 36' provided with a first axial bore 37 formed therein, and a male portion 38, 38' connected to the female portion 36, 36', respectively. Such a male portion 38, 38' axially protrudes outwardly away from the first axial bore 37. The second cord portion coupling 35 preferably includes a body 35a having a second axial bore 40 and a third axial bore 41 extending inwardly from proximal and distal ends thereof, respectively. The second axial bore 40 is spaced from the third axial bore 41. In this manner, the male portion 38, 38' of the first cord portion coupling 34, 34' is removably connected to the second axial bore 40 of the second cord portion coupling 35 such that alternate ones of the tip section 50 (i.e., snare member 70, 75, retrieval member 53, 54, 56, etc.) are selectively connected to the cord section 30 without having to discard the cord section 30 and the handle section 20. Such a structural configuration provides the unexpected and unpredictable advantage of enabling a user to swap tip sections 50 without having to acquire a complete new device 10 during operating procedures.

Referring to FIGS. 3-11b, in a non-limiting exemplary embodiment, the tip section 50 includes a tip section coupling 51 attached to a distal end of the second cord portion 32, and at least one of a retrieval member 53, 54, 56 and a snare member 70, 75 removably connected to the tip section coupling 51. Such a structural configuration provides the unexpected and unpredictable advantage of replacing only second portion 32 of cord section 30 when tip section 50 is changed.

In a non-limiting exemplary embodiment, exemplary retrieval members 53, 54, 56 include at least one basket selected from a group including a mesh basket 53 and a wire basket 54, 56, and an end cap 52 attached to a distal end of the wire basket 54, 56. Such a structural configuration provides the unexpected and unpredictable advantage of resiliently expanding and contracting the basket during removal/insertion processes.

In a non-limiting exemplary embodiment, exemplary wire baskets 54, 56 includes at least one of: a plurality of arcuate wires 55 engaged at opposed proximal and distal ends thereof such that the arcuate wires 55 form a bowed shape (as perhaps best shown in FIGS. 5-6); and a plurality of bent wires 65, 66, 67, 68 (FIG. 8) engaged at opposed proximal and distal ends thereof. Each of such bent wires 65, 66, 67, 68 has first, second and third linear sections 57, 58, 59 registered in respectively first, second and third paths 60, 61, 62 (illustrated via linear lines) in FIGS. 7 and 8) such that oppositely facing ones of the second linear sections 61 are registered parallel to each other (see FIG. 7), respectively. Such a structural configuration provides the unexpected and unpredictable advantage of accurately and efficiently expanded/contracting the wire basket during removal/insertion processes.

Referring to FIGS. 9-11a, in a non-limiting exemplary embodiment, exemplary snare members 70, 75 include at least one of: a plurality of elongated elements 71 conjoined at the tip section coupling 51 and spanning outwardly away therefrom wherein each of the elongated elements 71 has a loop 72 formed at a distal end of the tip section 50, and an elongated member 75 having a substantially oval shape wherein proximal and distal ends 76, 77 of the oval shape are pinched inwardly. Such a structural configuration provides the unexpected and unpredictable advantage of enabling a user to effectively squeeze the polyp and detach it from a support surface inside the patient.

The present discourse further includes a method of utilizing a snare and retrieval device 10 for removing an internal object from a patient. Such a method includes the chronological steps of: providing a handle section 20; providing and attaching a cord section 30 to the handle section 20; providing and removably attaching a tip section 50 to the cord section 30 such that the tip section 50 is spaced away from the handle section 20; and using the tip section 50 to detach a polyp from the patient. The method further includes the chronological steps of: selectively detaching the tip section 50 from the cord section 30 while the cord section 30 remains attached to the handle section 20; attaching an alternate one of the tip section 50 to the cord section 30; and using the alternate tip section 50 to retrieve the polyp from the patient. In this manner, the user does not have to obtain a complete new device 10 when switching out different tip sections 50 (i.e., snare member 70, 75, retrieval member 53, 54, 56, etc.)

In a non-limiting exemplary embodiment, the present disclosure makes the tip section 50 of the device 10 detachable that allows the surgeon to easily change the snare/retrieval member to a bigger or smaller size as necessary during the operation; or to exchange a snare member for a retrieval member, etc. This disclosure also allows the surgeon to use one cord section 30 for both removal of a polyp and retrieval of the polyp for further examination by histology. This is done by changing the snare member 70, 75 to a retrieval member 53, 54, 56, without having to obtain a complete new device 10. The detachability of the tip section 50 allows the device 10 to replace at least two or more separate snare and retrieval devices, thereby reducing cost and time during the operation. The cord section 30 and handle section 20 may be disposable or reusable after proper cleaning and sterilization.

In a non-limiting exemplary embodiment, tip section 50 may be manufactured from surgical grade steel and may measure ½" in length by 1/16" in width, with a tubular shape and a circumference of ⅜", for example. It is noted that the first and second cord portion couplings 34, 34' and 36, respectively, may be connected via a threaded screw fitting, a clip fastener or other suitably ways that removably attach the tip section 50 to the cord section 30.

In a non-limiting exemplary embodiment, a disposable fine, surgical steel loop 75 may be employed for snaring and removing lesions. Other configurations may include a variety of manually operated forceps, graspers and sterile plastic tips and be used only once and discarded. Easily attached to the cord section 30, routinely employed with colonoscopy endoscopes, the device 10 provides surgical quality instruments at a minimal expense, and can be disposable or reusable after proper cleaning and sterilization.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. § 1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A snare and retrieval device for removing an internal object from a patient, said snare and retrieval device comprising:
   a handle section;
   a cord section attached to said handle section; and
   a tip section being linearly and removably attached directly to said cord section and spaced away from said handle section;
   wherein said tip section is selectively detachable from said cord section while said cord section remains attached to said handle section;
   wherein said cord section includes a flexible cord having a first cord portion and a second cord portion spaced from said first cord portion;
   wherein said cord section further includes
      a first cord portion coupling being removably connected directly to a distal end of said first cord portion, and
      a second cord portion coupling being removably connected directly to said first cord portion coupling, said second portion coupling being removably connected directly to said second cord portion, respectively;
   wherein said second cord portion coupling is directly intercalated between said first cord portion coupling and said second cord portion.

2. The snare and retrieval device of claim 1, wherein said handle section comprises:
   a base member; and
   an elongated arm passing through said base member and connected to said cord section;
   wherein said elongated arm is linearly reciprocated relative to said base member and thereby causing linear reciprocation of said cord section and said tip section.

3. The snare and retrieval device of claim 2, wherein said cord section comprises:
   a flexible sheath removably mated to said base member and surrounding said first cord portion;
   wherein said first cord portion is connected to said elongated arm and is caused to linearly reciprocate within said flexible sheath when said elongated arm is linearly reciprocated through said base member.

4. The snare and retrieval device of claim 3, wherein said first cord portion coupling comprises:
   a body having a female portion provided with a first axial bore formed therein; and
   a male portion connected to said female portion, said male portion axially protruding outwardly away from said first axial bore;
   wherein said second cord portion coupling comprises
   a body having a second axial bore and a third axial bore extending inwardly from proximal and distal ends thereof respectively, said second axial bore being spaced from said third axial bore;
   wherein said male portion is removably connected to said second axial bore such that alternate ones of said tip section are selectively connected to said cord section without having to discard said cord section and said handle section;
   said first cord portion being removably and linearly attached directly to said first axial bore;
   said male portion being removably and linearly attached directly to said second axial bore;
   said second cord portion being removably and linearly attached to said third axial bore.

5. The snare and retrieval device of claim 4, wherein said tip section comprises:
   a tip section coupling being removably and linearly attached directly to a distal end of said second cord portion; and
   at least one of a retrieval member and a snare member removably connected to said tip section coupling.

6. The snare and retrieval device of claim 5, wherein said retrieval member comprises:
   at least one basket selected from a group including a mesh basket and a wire basket.

* * * * *